(12) United States Patent
Wavering et al.

(10) Patent No.: US 7,540,197 B2
(45) Date of Patent: Jun. 2, 2009

(54) SENSORS, METHODS AND SYSTEMS FOR DETERMINING PHYSICAL EFFECTS OF A FLUID

(75) Inventors: Thomas A. Wavering, Crozet, VA (US); Fritz J. Friedersdorf, Earlysville, VA (US); Nathan K. Brown, Palmyra, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 0 days.

(21) Appl. No.: 11/987,411

(22) Filed: Nov. 29, 2007

(65) Prior Publication Data

US 2008/0141780 A1    Jun. 19, 2008

Related U.S. Application Data

(60) Provisional application No. 60/861,981, filed on Dec. 1, 2006.

(51) Int. Cl.
*G01L 7/08* (2006.01)
(52) U.S. Cl. .......................................... 73/715
(58) Field of Classification Search ................... 73/716, 73/736
See application file for complete search history.

(56) References Cited

U.S. PATENT DOCUMENTS

| | | | |
|---|---|---|---|
| 5,301,001 | A | 4/1994 | Murphy et al. |
| 6,341,185 | B1 | 1/2002 | Elster et al. |
| 6,426,796 | B1 | 7/2002 | Pullman et al. |
| 6,571,639 | B1 | 6/2003 | May et al. |
| 6,671,055 | B1 | 12/2003 | Wavering et al. |
| 2007/0227252 | A1* | 10/2007 | Leitko et al. .................. 73/717 |

* cited by examiner

*Primary Examiner*—Andre J Allen
(74) *Attorney, Agent, or Firm*—Nixon & Vanderhye PC

(57) ABSTRACT

Sensors, methods and systems detect physical effects (e.g., corrosion, erosion, scaling and/or oxidation) of a fluid in contact with a diaphragm associated with a sensor assembly. The diaphragm preferably exhibits a first mechanical response when initially placed into contact with a fluid and a second mechanical response different from the first mechanical response after exposure to the fluid for a predetermined period of time. A change in the diaphragm mechanical responses between at least the first and second mechanical responses is therefore indicative of physical effects on the diaphragm over time caused by the fluid in contact therewith. A mechanical response sensor is operatively associated with the diaphragm so as to measure the change in the diaphragm mechanical responses and thereby determine the physical effects over time of the fluid in contact with the diaphragm. In some embodiments, the diaphragm is actuated due to a pressure condition exerted by the fluid or in other embodiments the diaphragm is internally actuated. Internal actuation includes pneumatic, hydraulic or piezoelectric means for producing a mechanical response of the diaphragm. In one embodiment, therefore, fluid corrosivity may be sensed by bringing a sensor assembly having a pressure-actuated diaphragm into contact with a corrosive fluid, exerting a pressure condition on the diaphragm so as to cause the mechanical response of the diaphragm, measuring the diaphragm deflection or strain, and then deriving fluid corrosivity from the measured diaphragm mechanical response.

53 Claims, 9 Drawing Sheets

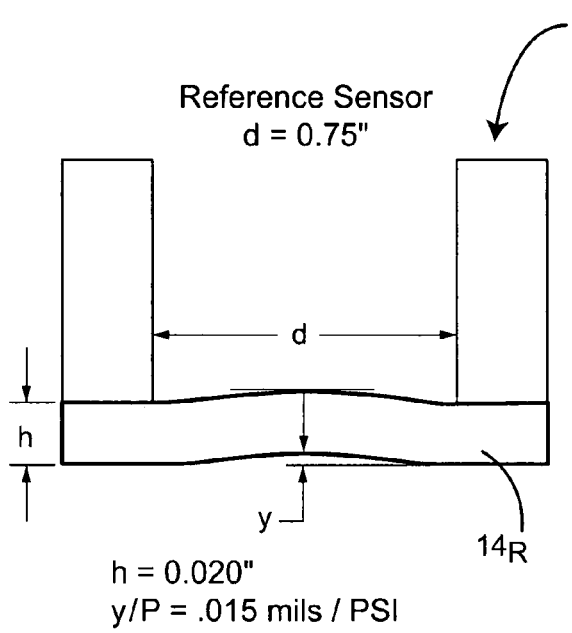
FIG. 2A
Reference Sensor
d = 0.75"
h = 0.020"
y/P = .015 mils / PSI
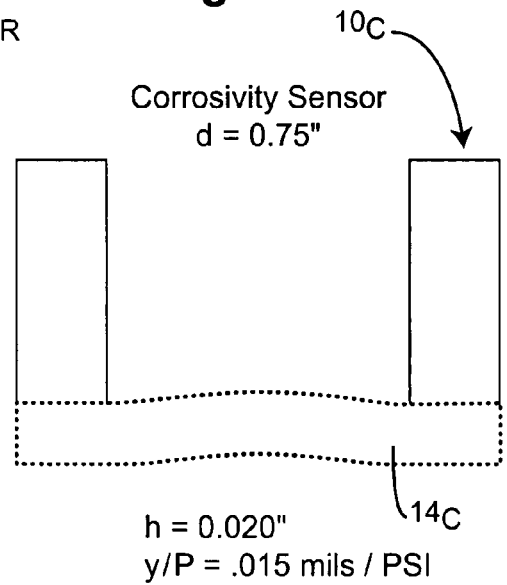
Fig2B
Corrosivity Sensor
d = 0.75"
h = 0.020"
y/P = .015 mils / PSI
FIG. 2C
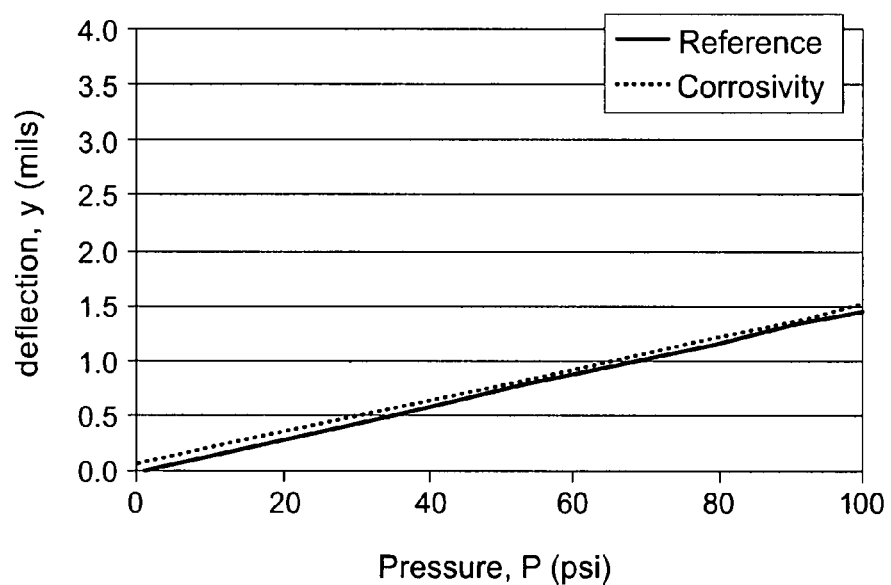

h = 0.020"
y/P = .015 mils / PSI

Diaphragm corrosion h = 0.015"
y/P = .035 mils / PSI

SENSORS, METHODS AND SYSTEMS FOR DETERMINING PHYSICAL EFFECTS OF A FLUID

CROSS REFERENCE TO RELATED APPLICATION

This application is based on and claims domestic priority benefits under 35 USC §119(e) from U.S. Provisional Patent Application Ser. No. 60/861,981 filed on Dec. 1, 2006, the entire content of which is expressly incorporated hereinto by reference.

GOVERNMENT RIGHTS STATEMENT

This invention was made with Government support under Grant No. W9132T-06-C-0017 awarded by the U.S. Army. The Government has certain rights in the invention.

FIELD OF INVENTION

The present invention relates generally to the field of sensors. In especially preferred embodiments, the present invention relates to sensors, methods and systems that my usefully be employed to detect the physical effects of a fluid (e.g., liquid, gas and multiphase media such as liquid slurries with suspended particulates) over time, such as the effects of corrosion, erosion, scaling and/or oxidation caused by the fluid. These detected physical effects of the fluid may then be used in appropriate systems to modify the fluid so it is less physically damaging to structural components (e.g., pipeline components, tanks, process vessels and the like) in contact with the fluid and/or to determine when structural components in contact with the fluid are in need of maintenance, repair, and/or replacement.

BACKGROUND OF INVENTION

In some engineering applications structural components are affected by the fluids they are in contact with. Example applications include all manner of chemical process equipment and piping systems, water treatment and distribution systems (industrial water and potable water systems, boiler systems and cooler systems, etc.) and oil and gas pipelines for collection, processing and distribution. In many of these applications, it is advantageous to monitor damage accumulation, predict component life, and control fluid properties to minimize damage to system structural components. Damage to structural components from fluids can include corrosion, erosion, scale and/or oxidation. Many structural components can be difficult to inspect, can be hidden from observation, can cause health and environmental damage in the event of failure, and/or can be costly to maintain. Advanced sensors are needed to actively monitor the physical effects of fluids in contact with structural components and minimize their deleterious effects. For example, physical effects sensors can be used as feedback in control systems for the injection of green treatment chemicals and corrosion inhibitors to control corrosion, biological growth, scaling in water treatment, chemical process and boiler systems. Advanced physical effects monitoring, such as corrosion, erosion, scale and/or oxidation, will result in reduced maintenance costs, increased component service life and safer operations.

A limited range of measurement technologies are conventionally utilized to determine the rate, type and physical effects that damage structural components, such as corrosion. These technologies can be grouped into two general categories, 1) metal loss and 2) electrochemical methods.

Metal loss measurement methods include mass loss coupons and electrical resistance devices. These techniques provide cumulative corrosion and possibly erosion, and corrosion rate data. Typically, the mass loss coupons are placed into the process stream or a side stream that can be accessed without process interruption. The coupons can be made of an alloy that is the same as the structural component being monitored, or can be a standard material including steels, stainless steel, copper and brass. Mass loss coupons are considered to be reliable for measuring corrosion over longer time periods at discrete intervals. To quantify corrosion, the mass loss coupons are retrieved cleaned and weighed. Mass loss coupons can be used in nearly any process, but do not allow for continuous monitoring, are labor intensive and require significant space within the process system or structure being monitored.

Electrical resistance sensors can continuously monitor cumulative corrosion and possibly erosion and corrosion rate of metal elements. The principle of operation of resistance sensors is measurement of ohmic losses as the cross section of the sensing element decreases due to corrosion. The resolution and service life of the resistance probes vary based on sensor thickness with the highest resolution achieved at the expense of sensor life. The more sensitive resistance probes have response times of about 100 hours for corrosion rates of 1 MPY. Resolution is reduced by thermoelectric voltages and electromagnetic noise. Resistance probes provide for continuous monitoring without process interruption and function in virtually any environment, except molten metal and conductive molten salts. The metal loss methods provide data in environments where fouling occurs, although the fouling may effect the corrosion rate and mode of attack (under deposit corrosion).

Electrochemical methods, including Linear Polarization Resistance (LPR), Electrochemical Impedance Spectroscopy (EIS) and Electrochemical Noise (EN) are used to monitor corrosion. These measurement techniques are used to quantify the thermodynamics and kinetics of electrochemical reactions associated with corrosion. LPR is used extensively to detect instantaneous corrosion rates, but application is limited to conductive solutions and performance is restricted in low conductivity waters and non-aqueous environments. Like resistance sensors, the resolution of electrochemical methods is reduced by thermal and electromagnetic noise. Unlike resistance and mass loss coupon methods, electrochemical techniques are unable to detect metal loss due to erosion, or to provide a direct measure of cumulative material loss. Furthermore, electrode fouling limits the use of LPR and if fouling does occur the sensors are removed, cleaned and possibly returned to service. Electrochemical methods may require specialist knowledge for data interpretation.

A variety of fiber-optic sensors based on Extrinsic Fabry-Perot Interferometric (EFPI) technology are known as disclosed in U.S. Pat. Nos. 5,301,001; 6,341,185; 6,426,796 and 6,571,639, the entire content of each such prior-issued patent being expressly incorporated hereinto by reference. In general, the Extrinsic Fabry-Perot Interferometric (EFPI) technology measures distance based on a low-finesse Fabry-Perot cavity formed between the polished end face of a fiber and a reflective surface.

There exists a need in the art, therefore, for reliable sensors that may be used for the continuous detection of fluid effects on structures and/or components in contact with the fluid. Further, there is a need for physical effects sensors that may have long service life, that may detect cumulative damage and damage rates, and may be compatible with automated monitoring and control systems. It is towards fulfilling such needs that the present invention is directed.

SUMMARY OF INVENTION

According to the present invention, a change in mechanical response of a diaphragm when actuated is used to monitor total change in diaphragm thickness and rate of change in thickness so as to sense the physical effects of a fluid in contact with the diaphragm. Exemplary physical effects caused by fluid contact that can be detected with the sensors of the present invention include, for example, corrosion, erosion, scaling and/or oxidation of the diaphragm.

The range and sensitivity of the sensors may be tailored by the diaphragm geometry (thickness and diameter), alloy selection, and the mechanical properties of the diaphragm (Young's modulus and Poisson's ratio). Sensitivity to physical effects being detected may also be achieved by selecting metals and alloys with known properties, such as corrosion or erosion properties, to use as the sensor diaphragm. These diaphragm materials may be the same as the structural component in which the sensor is intended to be employed (e.g., a chemical process system, tank, pipeline or the like) or have a similar response (e.g., corrosion rate) that correlates to the structural component being monitored.

As used herein and in the accompanying claims, the term "mechanical response" is intended to mean a change in deflection, strain and/or natural frequency of the diaphragm. Thus, by measuring any combination of these mechanical responses, a measurement of corrosivity, erosion, scaling and/or oxidation can be derived using a variety of conventional mechanical response sensors (e.g., optical, electrical, piezoelectric and like means). Additionally, the change in mechanical response of the diaphragm is measured by actuating the diaphragm. Diaphragm actuation may be passive and due to external causes, such as fluid pressure, e.g., process pressure. Internal active actuation mechanisms can also be used to deflect, strain, and/or vibrate the diaphragm.

By way of example, if fluid corrosion is being monitored, then such corrosion causes the diaphragm to thin which consequently alters the mechanical response (e.g., deflection, strain or resonant frequency characteristics) of the diaphragm relative to a non-corroding reference sensor or some baseline condition. Detection of the change in the mechanical response of the diaphragm when actuated (e.g., by means of the fluid pressure in contact with the sensor) will thus enable measurement of corrosion rate and cumulative corrosion damage.

The mechanical response of the diaphragm can be monitored using a variety of conventional sensors, including optical, electrical, piezoelectric, and acoustic techniques. Preferably, the diaphragm pressure response is monitored by either fiber optic displacement techniques or electrical resistive strain gage techniques.

The sensor of the present invention is applicable in both open and closed systems that include chemical process systems, water pipeline systems, tanks and reactor vessels, a broad range piping and conduit systems that carry liquid (water, fuel, oil, etc), gas and multiphase (mixtures of liquid, gas, and solid phases) flows. The sensors of the present invention are applicable in systems used in potable and industrial water, electric power generation, chemical, pulp and paper, heat exchanger, incinerator and fossil fuel applications. In addition, the sensors of the present invention may be employed satisfactorily to detect erosion caused, for example, by a fluid (e.g., liquid or gas) that may have suspended particulate matter. Scaling deposits and/or high temperature oxidation caused by a fluid may also be monitored using the sensors of the present invention.

For ease of discussion, the physical effects sensors of the present invention will be referenced below as being usefully employed as a corrosivity sensor so as to detect fluid corrosion attributes. However, it will be understood that this represents a presently preferred embodiment of the invention which is non-limiting with respect to the same. Further, a preferred embodiment of the sensors is based on fiber-optic detection means. Similarly, another preferred embodiment of the sensors is based on semiconductor based resistive strain gage detection means. As described previously, other suitable detection means may be employed satisfactorily and thus reference to fiber-optic based and semiconductor resistive strain gage based sensors is exemplary only of presently preferred embodiments and thus non-limiting with respect to the same.

According to some embodiments, therefore, a sensor assembly is provided for determining physical effects over time of a fluid in contact with the sensor. The sensor assembly will preferably include a diaphragm which exhibits a first mechanical response characteristic when initially placed into contact with a fluid and a second mechanical response characteristic different from the first mechanical response characteristic after exposure to the fluid for a predetermined period of time. A change in the mechanical response characteristics of the diaphragm between at least the first and second mechanical response characteristics is therefore indicative of the physical effects on the diaphragm over time caused by the fluid in contact therewith. A mechanical response sensor is operatively associated with the diaphragm so as to measure the change in diaphragm mechanical response characteristics and thereby determine the physical effects over time of the fluid in contact with the diaphragm.

Thus, in the context of a corrosivity sensor, a preferred embodiment will comprise a diaphragm which is susceptible to corrosion when placed in contact with a fluid, the diaphragm having a first mechanical response characteristic of deflection in response to an external pressure condition exerted on the diaphragm by the fluid. The extent to which the diaphragm deflects will therefore increase in response to corrosion of the diaphragm by the fluid (e.g., due to a thinning of the diaphragm by corrosion which allows it to be mechanically deflected to a greater extent as compared to the non-corroded condition). A deflection sensor will therefore be operatively associated with the diaphragm so as to measure an increase in the deflection relative to the nominal deflection thereof which is indicative of the fluid corrosivity.

Further, in the context of a corrosivity sensor, a preferred embodiment will comprise a diaphragm which is susceptible to corrosion when placed in contact with a fluid, the diaphragm having a first mechanical response characteristic of strain in response to an external pressure condition exerted on the diaphragm by the fluid. The extent to which the diaphragm strains will therefore increase in response to corrosion of the diaphragm by the fluid (e.g., due to a thinning of the diaphragm by corrosion which allows it to be mechanically strained to a greater extent as compared to the non-corroded condition). A strain sensor may therefore be operatively associated with the diaphragm so as to measure an increase in the strain relative to the nominal deflection thereof which is indicative of the fluid corrosivity.

BRIEF DESCRIPTION OF THE DRAWINGS

These and other features and advantages will be better and more completely understood by referring to the following detailed description of exemplary non-limiting illustrative embodiments in conjunction with the drawings of which:

FIGS. 2A and 2B respectively depict a reference sensor and a corrosivity sensor of a sensor assembly of the present invention in the first condition of a non-corroded state;

FIG. 2C is a plot of diaphragm mechanical response e.g. deflection (mils) versus pressure (psi) for the reference sensor and corrosion sensor in the first condition of a non-corroded state depicted in FIGS. 2A and 2B;

DETAILED DESCRIPTION

Figure 1:
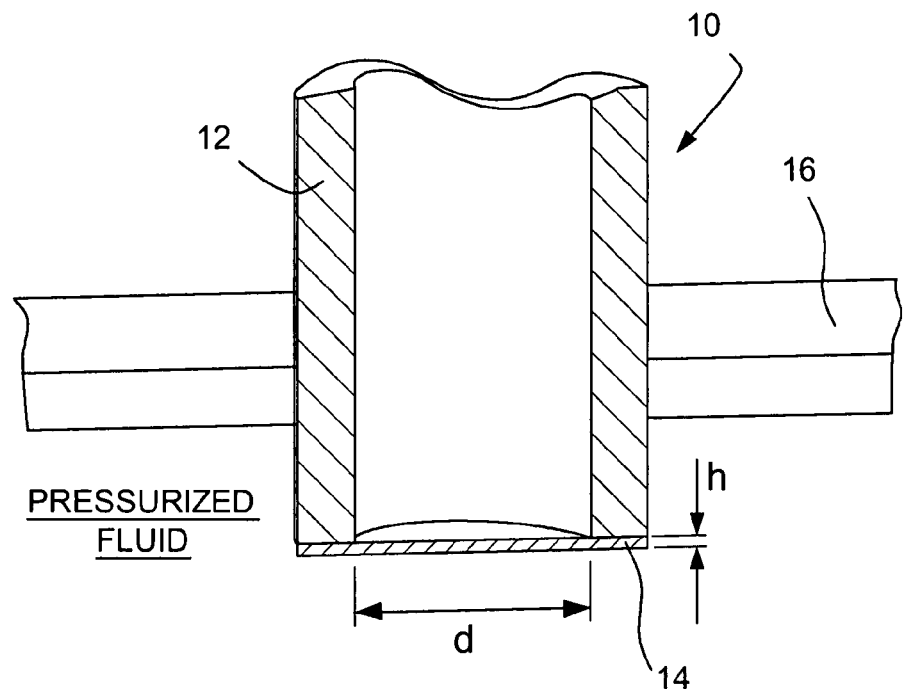
FIG. 1 is a schematic cross-sectional view of a sensor positioned in a pipe wall so that the diaphragm of the sensor is in contact with a pressurized fluid flowing within the pipe interior.

As shown in FIG. 1, a physical effects sensor 10 having a housing 12 and a diaphragm 14 at a distal end of the housing 12 may be positioned in a structural component such as a tank or pipe 16 containing a pressurized fluid (e.g., liquid, gas, and/or multiphase) whose effects are to be monitored. As such, the diaphragm 14 is in contact with the fluid within the structural component 16. The diaphragm 14 will have a sensing diameter d and a substantially constant thickness h. When employed as a corrosivity monitor, the diaphragm 14 is preferably constructed from a material that corrodes at a similar rate as the material of the structural component 16, or whose damage rate correlates to the material of the structural component 16. Different metal diaphragms can be selected for the specific structural component or process system application and environmental, e.g., fluid conditions of interest.

Figure 1A:
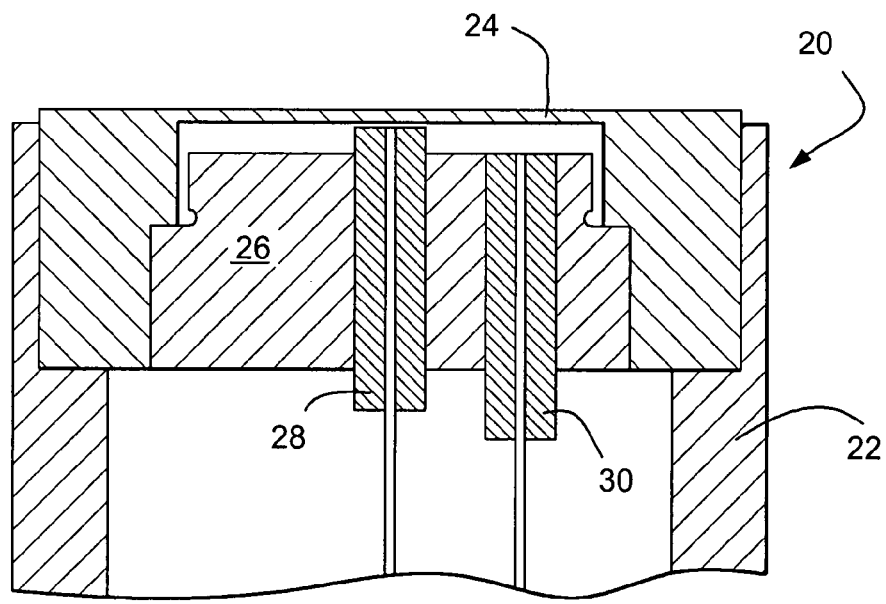
FIG. 1A is an enlarged cross-sectional view of the terminal end of a sensor according to one embodiment of the invention.

Accompanying FIG. 1A shows in greater detail a possible physical effects sensor assembly 20 in accordance with the present invention. As shown, the physical effects sensor 20 includes a housing 22 having an integral machined diaphragm 24 fabricated from a material whose corrosion is to be measured that is positioned at the housing's distal end. A fixturing plug 26 is mounted to an interior side of the diaphragm 24 for maintaining the fiber optic deflection sensor 28 and a temperature sensor 30 in proximity to the back side of the diaphragm 24. As shown, the fixturing plug 26 defines an air-filled space 32 with the back side of the diaphragm 24 which serves as a medium to allow the temperature sensor 30 to sense diaphragm temperature conditions.

Potential diaphragm materials for the corrosivity sensors in accordance with the present invention include but are not limited to typical engineering alloys such as steel, stainless steel, copper, nickel alloys and brass. The pressure sensitivity of the diaphragm (i.e. deflection or strain response to pressure) is dictated primarily by the diaphragm geometry and material properties: diameter, d, thickness, h, elastic modulus, E, Poisson's ratio, $\mu$, and constant of proportionality, K that is dependent on strain gage orientation and location on the diaphragm. Theoretically, the diaphragm displacement sensitivity (y/P) or strain sensitivity ($\epsilon$/P) are given by the following formulas when operating within the linear region (y/h<0.3):

$$\frac{y}{P} = \frac{3(1-\mu^2)d^4}{256Eh^3} \qquad \text{EQUATION 1}$$

$$\frac{\epsilon}{P} = \frac{d^2}{Eh^2}K \qquad \text{EQUATION 2}$$

Figure 2D:
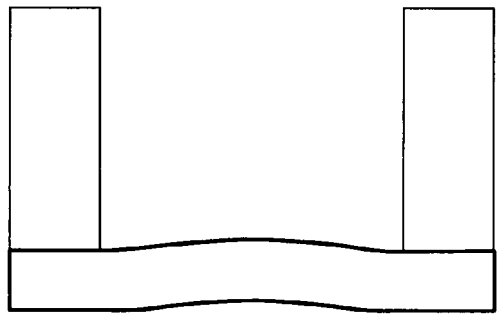
FIGS. 2D and 2E show the reference sensor and the corrosion sensor depicted in FIGS. 2A and 2B in the second condition after exposure to a corrosive fluid.

Given the high-order dependence of displacement and strain on diaphragm thickness ($h^{-3}$ for displacement, $h^{-2}$ for strain), the response of the physical effects sensor of the present invention is very sensitive to thickness changes, especially when the initial thickness is small. Therefore, cumulative corrosion of the diaphragm material can be precisely monitored by measuring its response to the internal pressure of a structure such as pipeline or tank as shown in FIGS. 2A through 2E. In this regard, it will be observed in FIGS. 2A and 2B that the reference and corrosivity sensors 10R and 10C are each provided with a respective diaphragm 14R and 14C, respectively having similar physical characteristics. Thus, the mechanical response to pressure, or the deflection of the diaphragms 14R and 14C will be substantially the same in the first condition as shown by the graph of FIG. 2C before corrosion.

Figure 2E:
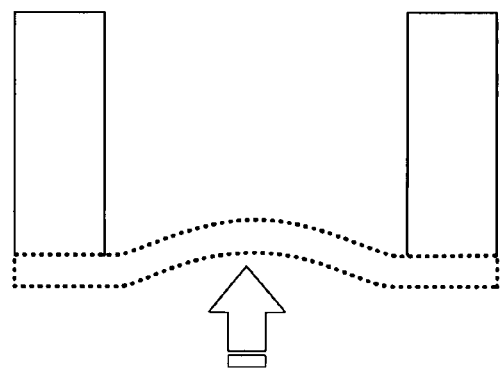
Figure 2F:
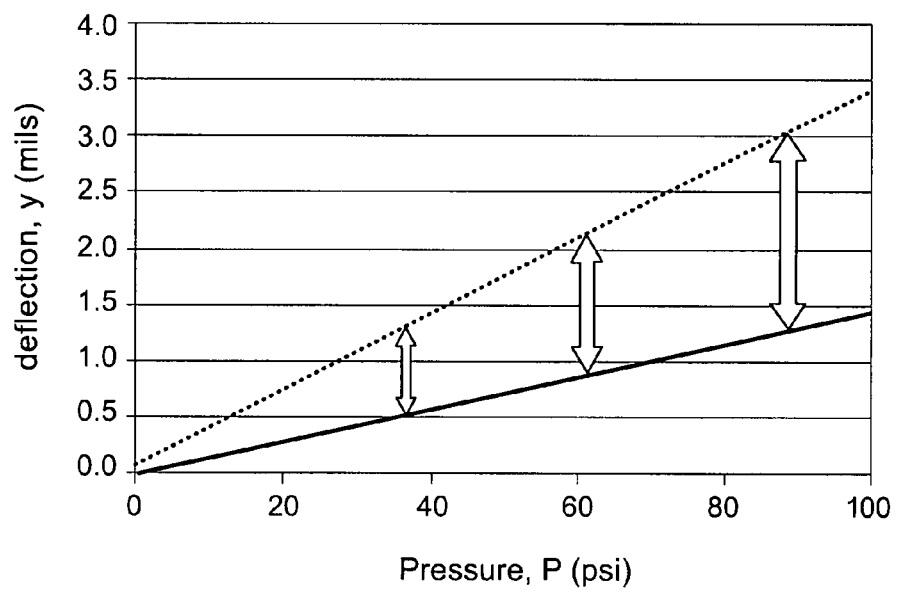
FIG. 2F is a plot of diaphragm mechanical response e.g. deflection (mils) versus pressure (psi) of the reference sensor and corrosivity sensor in the second condition after exposure to a corrosive fluid depicted in FIGS. 2D and 2E.

The reference diaphragm 14R is however formed of a material that resists corrosion from the fluid or other wise protected as with a coating. The diaphragm 14C is formed of a material that is susceptible to physical effects by the fluid such as corrosion. FIGS. 2D and 2E therefore depict the diaphragm 14R associated with the reference sensor 10R and the diaphragm 14C associated with the corrosion sensor 10C after being exposed to a fluid which has caused a physical effect such as thinning of the diaphragm 14C by 0.005 inch as compared to the diaphragm 14R. As such, diaphragm 14C exhibits substantially greater mechanical response or deflection as compared to the diaphragm 14R as depicted in FIG. 2F. This mechanical response difference can therefore be monitored for given pressure conditions to determine corrosivity of the fluid in contact with the diaphragm 10C.

The physical effects of the fluid on the sensor diaphragm can be ascertained using several embodiments including (A) a passive external actuation embodiment, (B) an active internal actuation embodiment. The active internal actuation embodiment could include actuation by pneumatic, hydraulic, and electromagnetic means such piezoelectric and/or solenoid actuators. Further, a preferred embodiment is the passive external actuation of the diaphragm of the physical effects sensor by the fluid pressure.

Both active and passive actuation of the diaphragm produce mechanical responses of the diaphragm. The mechanical response produced by diaphragm actuation includes diaphragm deflection, strain and/or resonance. These mechanical responses can be measured using a variety of conventional techniques such as electrical, piezoelectric, optical or acoustic approaches. A preferred embodiment is the use of an Extrinsic Fabry-Perot Interferometric fiber optic displacement sensor to measure diaphragm displacement. Further, another preferred embodiment is the use of resistive strain gages such as foil or semiconductor type to measure the diaphragm strain.

Figure 3A:
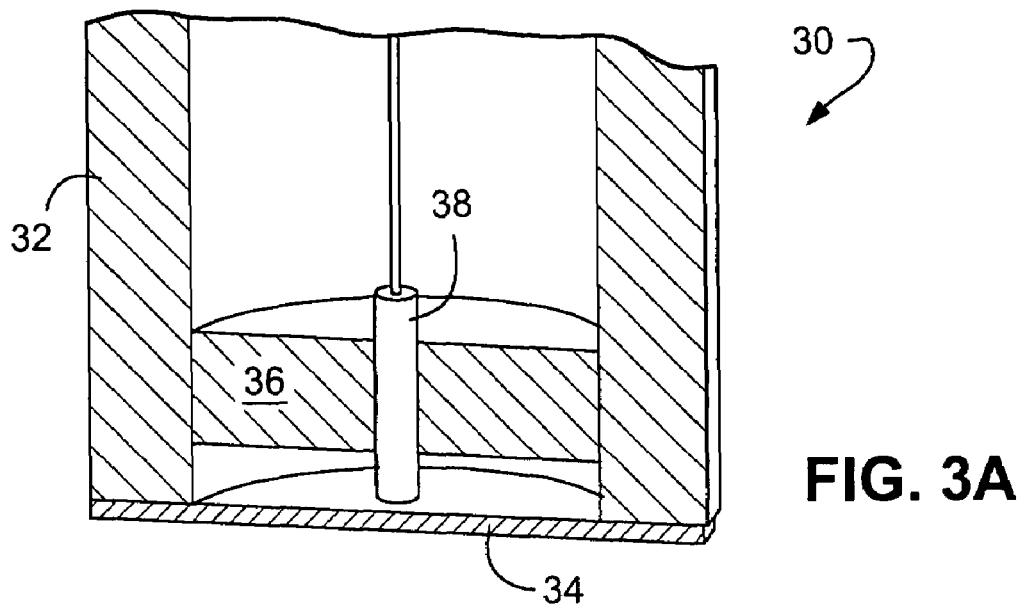
FIGS. 3A and 3B are cross-sectional views of sensors embodying a fiber-optic based diaphragm deflection sensor and an electrical strain gage based diaphragm deflection sensor, respectively.

A fiber optic based embodiment of a physical effects sensor 30 is depicted in FIG. 3A having a housing 32, a diaphragm 34 attached to the distal end of the housing 32 and a fixture plug 36 for positioning and maintaining a fiber optic sensor 38 in proximity to the diaphragm 34. This Extrinsic Fabry-Perot Interferometric fiber optic sensor monitors the central deflection of the diaphragm with interferometric precision of approximately 1 nanometer, which provides for a very high resolution diaphragm thickness measurement.

Figure 3B:
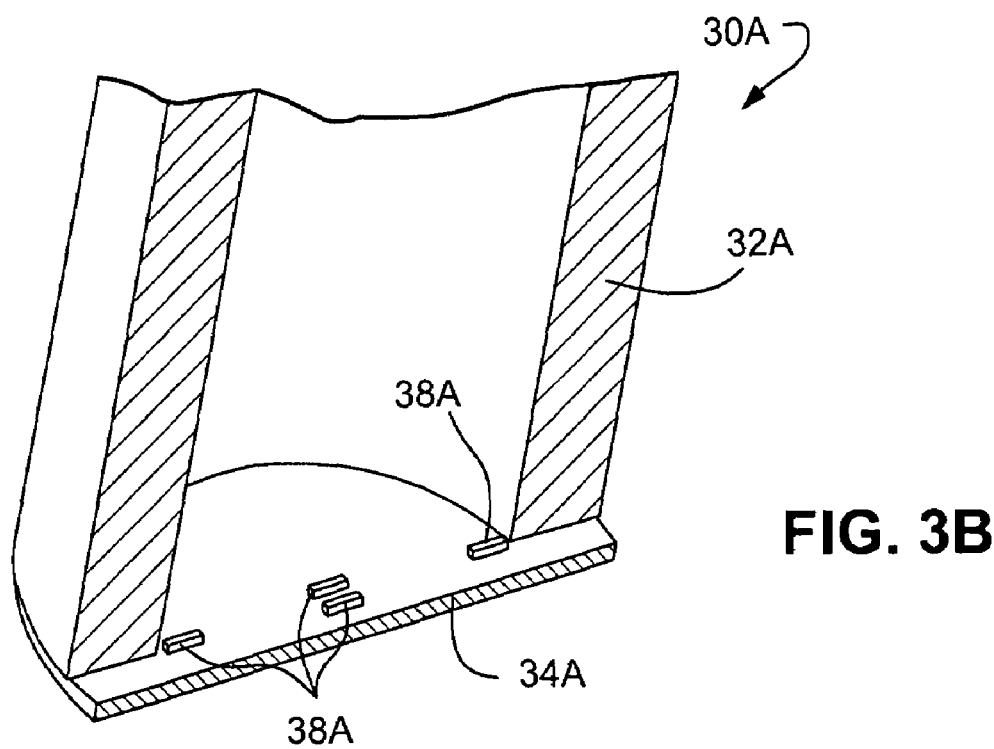

Another embodiment of a physical effects sensor 30a is depicted in FIG. 3B having a housing 32A, a diaphragm 34A attached to the distal end of the housing 32A and a plurality of strain gages 38A positioned on a back side of the diaphragm 34A. The strain gages 38A mounted to the back of the diaphragm 34A. In this embodiment, the strain gages serve to capture the strain response of the diaphragm to the fluid pressure 34A. Using highly sensitive strain gages, such as semiconductor-based gages, yields a very fine resolution of the diaphragm thickness.

For a given sensor geometry, increasing pressure generates more diaphragm deflection and strain, and therefore produces a finer resolution on the diaphragm thickness loss measurement. The sensor resolution and service life are inversely related and are controlled through diaphragm design and dependent on the expected corrosion (damage) rates. The preferred embodiment of a corrosivity sensor is actuated by the fluid pressure in the pipeline without need for further mechanisms.

The accuracy of the physical effects sensor can be further improved by the use of a reference sensor. The reference and physical effects sensors are located in close proximity to each other such that they are subject to similar fluid conditions. The reference sensor is used to remove other environmental effects such as temperature to obtain a precise measurement of the mechanical response that can be used to quantify diaphragm thickness and therefore corrosion, erosion, scale and/or oxidation of the diaphragm.

By comparing the physical effects sensor and reference sensor response to actuation such as fluid pressure transients, the thickness of the physical effects sensor diaphragm may be calculated using a mechanics analysis. This technique is equally applicable for mechanical response sensors that measure diaphragm deflection or stain.

As was shown previously by FIGS. 2C and 2F, the reference sensor provides a measurement with constant mechanical response sensitivity; while the mechanical response sensitivity of the corroding diaphragm changes with physical effects to the diaphragm due to contact with the fluid. In the case of corrosion, deflection or strain sensitivity increases as material is removed from the diaphragm. In one embodiment, the reference sensor could be provided by a commercially available pressure probe located near the corrosivity sensor in the process stream. A preferred embodiment of the reference sensor of the present invention is a sensor constructed similar to the corrosivity sensor, except that its diaphragm is protected from the fluid. In this embodiment, protection is accomplished by coating or covering the diaphragm with a material that produces a barrier between the diaphragm and the fluid. The barrier is thin and does not substantially alter the mechanical response of the reference sensor. Barrier materials may be coatings or sleeves or coverings of organic and polymeric materials, such as a polyurethane, epoxy, or fluorocarbon (PVDF). In another preferred embodiment, the reference diaphragm is made of a more inert material than the corrosivity sensor. The inert material is chosen for resistance to the physical effects from the fluid and may include non-metals such as glass or ceramics and metals and alloys such as steels, stainless steels, brass, copper, aluminum alloys, and nickel based alloys. Extraneous environmental effects, such as temperature affect both the reference and corrosivity sensors in the same manner. Comparing the response of the reference and corrosivity sensors therefore provides a measurement of the physical effects such as corrosion while being robust to other extraneous environmental factors. Additional thermal compensation may be a benefit for measurement resolution, especially for the strain gage sensor embodiment that may have slightly different thermal response between the reference and corrosivity sensors.

Another embodiment of the present invention is an active internally actuated physical effects sensor. The actuated physical effects sensor uses a built-in means for actuating the diaphragm. The active internal actuation embodiment would include actuation by pneumatic, hydraulic, and electromagnetic means such piezoelectric and/or solenoid actuators. A preferred embodiment of a sensor actuated diaphragm technique is the application of gas pressure to the backside of the diaphragm. Another preferred embodiment is the actuation of the diaphragm directly from the backside of the diaphragm using a device such as a piezoceramic actuator or solenoid.

The internally actuated physical effects sensor utilizes the same diaphragm mechanical response measurement strategies as the passive externally actuated physical effects sensor (i.e. EFPI, strain gage). The physical effects sensor diaphragm mechanical response would be determined by measuring the diaphragm response to the applied actuation such as force, pressure or displacement. One benefit of this embodiment of the physical effects sensor is that the internally actuated physical effects sensor of the present invention could be used in a broader range of applications since no external pressure from the fluid is required for sensor actuation and function.

In another embodiment of the active internally actuated physical effects sensors, resonant frequency-based physical effects sensors utilize the natural frequency of a diaphragm that is dependent on the diaphragm mass and stiffness. Theoretically, the natural frequency ($f_n$) of a round diaphragm clamped at the edges is given by:

$$f_n = \frac{36.9}{\sqrt{1+\beta}} \frac{h}{d^2} \left( \frac{E}{w(1-\mu^2)} \right)^{1/2} \qquad \text{EQUATION 3}$$

where h is diaphragm thickness, w is the diaphragm material density, and β is a constant that is proportional to the density of the fluid. From this relationship, it is clear that the natural frequency is proportional to the diaphragm thickness, holding all the other variables constant. Therefore, by accurately measuring the change in diaphragm natural frequency, the diaphragm thickness loss can be determined.

The natural frequency of a system can be determined by applying a sinusoidal excitation to the system over a range of frequencies while observing the magnitude and phase of the response at each frequency. The natural frequency is characterized by the frequency with the maximum amplitude.

A piezoelectric force actuator paired with a strain gage is one embodiment that can be used to apply a sine-sweep measurement to determine the natural frequency of the sensor diaphragm. The actuator applies the sinusoidal excitation force to the diaphragm, and the diaphragm strain response is detected with the strain gage. The achievable diaphragm thickness resolution is dependent on the ability of the sensing system to measure the shift in natural frequency. A benefit of the natural frequency based sensing method is that a fluid pressure is not required for measurement of the physical effect. Precise measurement of the applied excitation force amplitude is not required nor an absolute measure of the amplitude response since the physical effect measurement is based on resonance frequency.

The physical effects sensor has an additional advantage of being compatible with electrochemical methods used to quantify corrosion rates. These electrochemical methods include Linear Polarization Resistance (LPR), Electrochemical Impedance Spectroscopy (EIS), galvanic current measurements with a zero resistance ammeter (ZRA), and Electrochemical Noise (EN). By making an electrical connection through the sensor body to the diaphragm, the diaphragm can be used as the working electrode of an electrochemical cell arrangement. Simple two electrode or three electrode configurations can be used in conjunction with electrochemical test equipment and analysis techniques to obtain LPR, EN, galvanic current, and EIS measurements.

Figure 4:
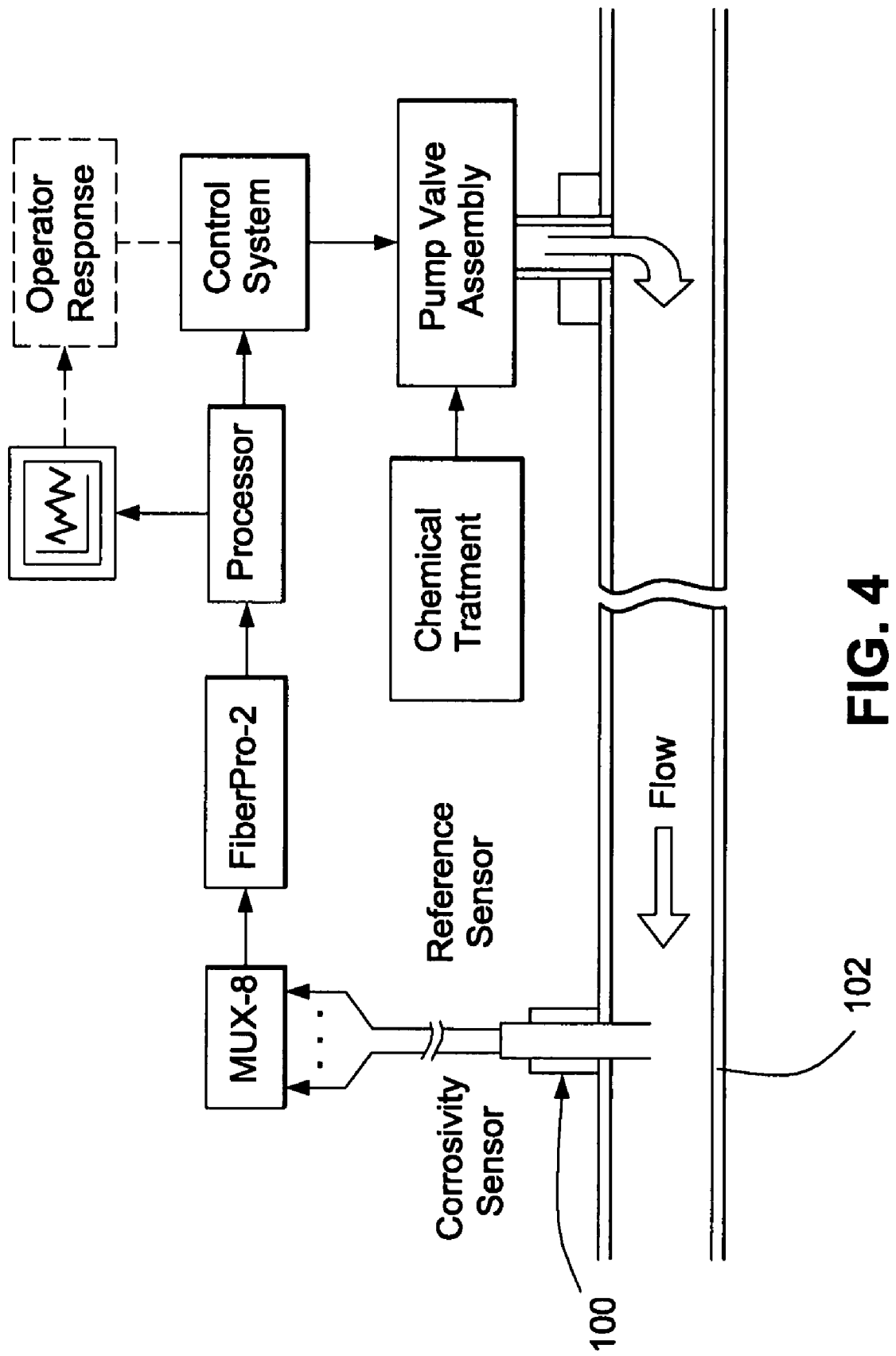
FIG. 4 is schematic diagram of a corrosivity sensing system for diagnostic monitoring and feedback control of a fluid treatment system.

As depicted in FIG. 4, a physical effects sensor assembly 100 comprised of a corrosivity sensor and a reference sensor as described previously may be provided as a part of an automated process control system where process chemistry, inhibitors, or environmental conditions are altered to maintain preset conditions of a fluid flowing within a pipe 102. As shown, the physical effects sensor 100 provide information through wired or wireless means to a processor that determines whether there is any deviation from a preset condition established for the fluid within the pipe 102. If deviation is detected, then the processor may output a signal to a controller that serves to operate a pump/valve assembly to inject suitable chemical treatment into the fluid.

A further understanding of this invention will be achieved by the nonlimiting Examples below.

EXAMPLES

The results of testing in flow cells clearly demonstrated the functionality of the herein disclosed physical effects sensors for monitoring corrosivity of flowing water systems. Through this testing, the following significant attributes have been demonstrated:

Sensors integrated into corporation stops and evaluated under representative conditions for water systems,
Repeatable measurement of mechanical response in pressurized fluid,
Using a reference sensor the mechanical response sensitivity was independent of other environmental factors such as temperature,
Mechanical response sensitivity measured using optical fiber sensors was a strong function of the cumulative corrosion of the diaphragm, and
One to one relationship and excellent correlation ($R^2>0.99$) between the electrochemical Faraday's Law calculations and the measured thickness based on a mechanics model of the physical effects sensor response.

Non-Corrosion Environmental Compensation Testing

Figure 5:
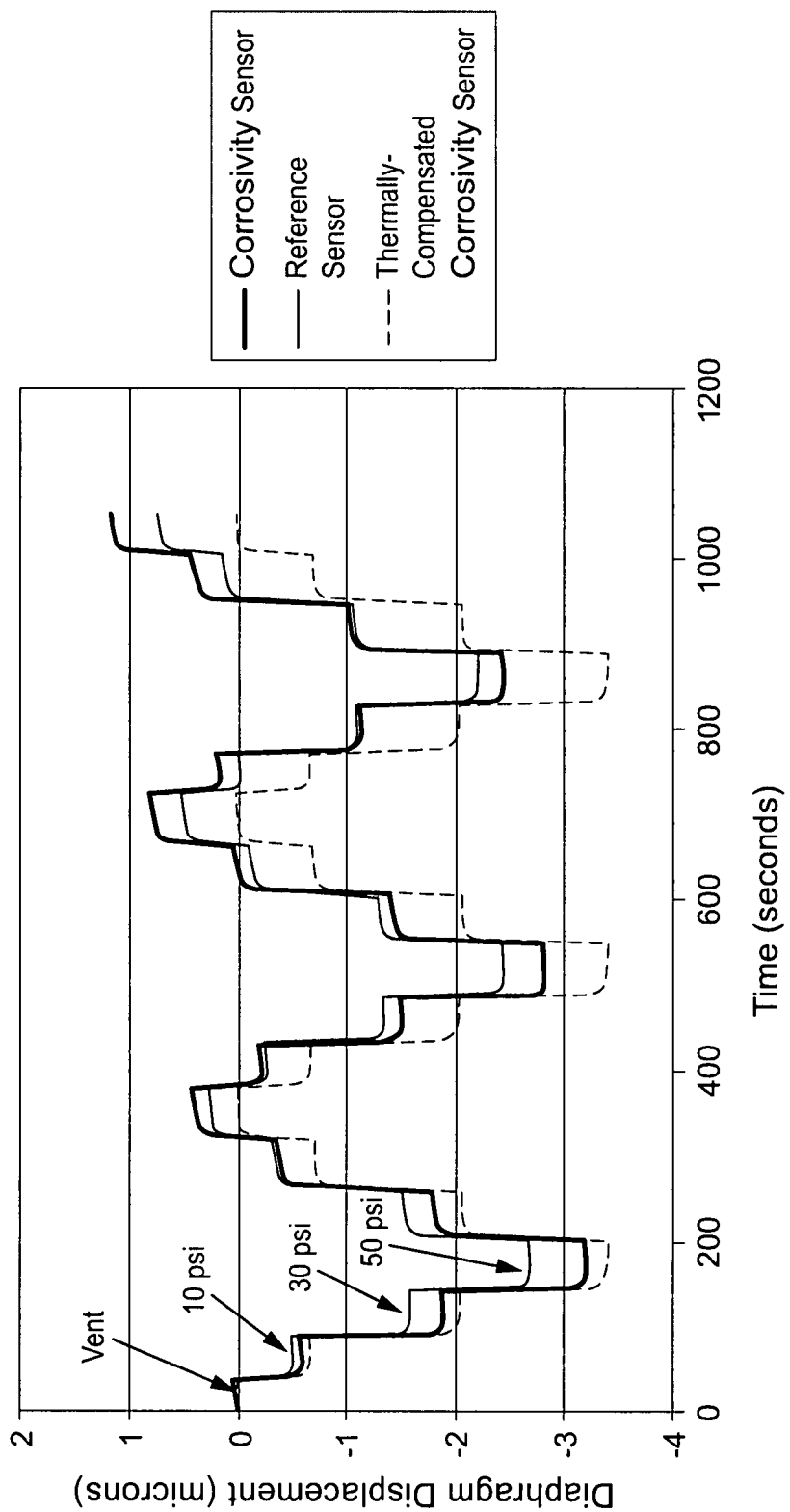
FIG. 5 is a plot of diaphragm displacement (microns) versus time (seconds) showing the response of the corrosivity sensor, reference sensor and thermally compensated corrosivity sensor to a pressure cycle under fluid flow conditions.

This series of tests evaluated the ability to use the response of the reference sensor to compensate for thermal and other environmental effects, other than corrosion, on the physical effects or corrosivity sensor. First, the thermal sensitivity of both the corrosivity sensor and reference sensors were evaluated by exposing them to a high flow environment for an extended period of time which resulted in a gradual increase in temperature of the flow loop solution (deionized water). Both sensors exhibited a linear response to temperature and a thermal scaling factor to remove any variances in thermal sensitivity was calculated. Next, the sensors were cycled under pressure over the pressure range of vent, 10, 30, 50, 30 psig, etc as shown in FIG. 5. Clearly both test and reference sensors exhibited thermal drift. However, through the use of the thermal scaling factor and the response of the reference sensor, this thermal drift can be eliminated as shown in the graphed response of the thermally compensated corrosivity sensor.

Corrosivity Sensor Response with Applied Current

This series of tests with the corrosivity sensors and flow loop setup were performed to evaluate the sensors ability to measure changes in diaphragm thickness over a range of applied corrosion currents. The diaphragm was corroded by anodically polarizing the diaphragm relative to a graphite counter electrode located in the flow loop solution (deionized water solution with 5 wt % $FeCl_3$).

The corrosivity and reference sensors were fabricated using machined acrylic housings. The mechanical response of the diaphragms was monitored by measuring the deflection with 830 nm single mode optical fiber using the Extrinsic Fabry-Perot Interferometric technique. The steel diaphragms were attached to an acrylic housing an epoxy adhesive. Corrosivity and reference sensors were designed to be compatible with commercially available corporation stops for introduction into the pressurized fluid. The sensors were monitored and the data was acquired with a FiberPro 2 system commercially available from Luna Innovations Inc. of Roanoke, Va.

The diaphragms used for this example provide a reasonable balance between sensitivity and lifetime. The diaphragms are 10 mm diameter, 0.020" thick, cold rolled hard, SAE/AISI 1010 shim steel. The surfaces were lightly sanded with 600 grit abrasive paper. The physical effects corrosivity sensor was used in the clean bare metal condition and the reference sensor was polymer coated with a solvent borne lacquer. The edge of the metal diaphragm of the corrosivity sensor was masked with a silicone RTV sealant. These sensors were small enough to fit into commercially available pipe fixtures, such as a corporation stop.

The diaphragm of the corrosivity sensor was polarized using a programmable power supply and the current was recorded with a digital multimeter with continuous data acquisition. An electrical lead required to apply the potential to the steel diaphragm was soldered to the external surface of the steel diaphragm and routed back through the body of the corrosivity sensor parallel to the optical fiber. The connection point for the lead on the steel diaphragm was protected from the electrolyte by silicone RTV sealant. The connection point was also along the outer edge of the diaphragm so it was mechanically isolated from the deflecting area of the diaphragm. The current was continuously recorded and the current density was calculated from the approximated diaphragm area exposed to the fluid electrolyte.

Figure 6:
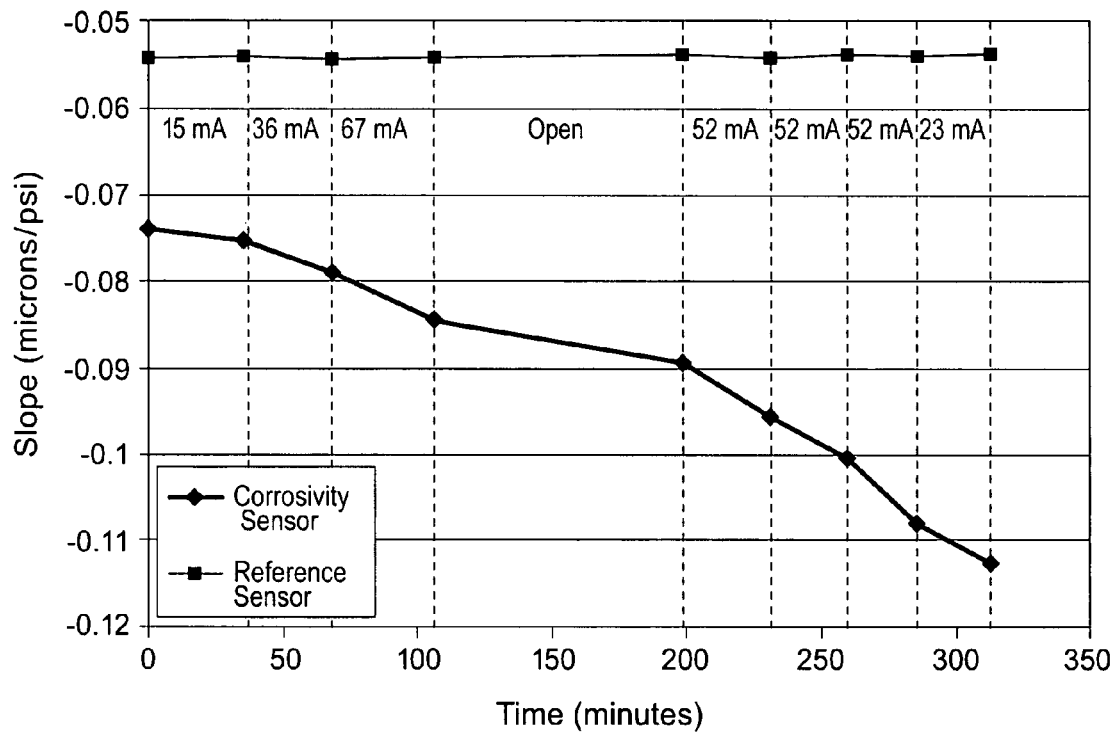
FIG. 6 is a plot of the slope (microns/psi) versus time (minutes) showing the change in pressure measurement sensitivity of a test corrosivity sensor and a reference sensor to different applied corrosion rates.

Thickness was calculated from the corrosivity sensor response using the following equation:

$$h = \sqrt[3]{\frac{3d^4(1-\mu^2)}{256E}} M \qquad \text{EQUATION 4}$$

Where h and d are diaphragm thickness and radius, respectively, $\mu$ is Poisson's ratio for the diaphragm, E is Young's modulus of elasticity for the diaphragm material, and M is the pressure sensitivity ratio (deflection/pressure) that was determined experimentally (FIG. 6).

Figure 7:
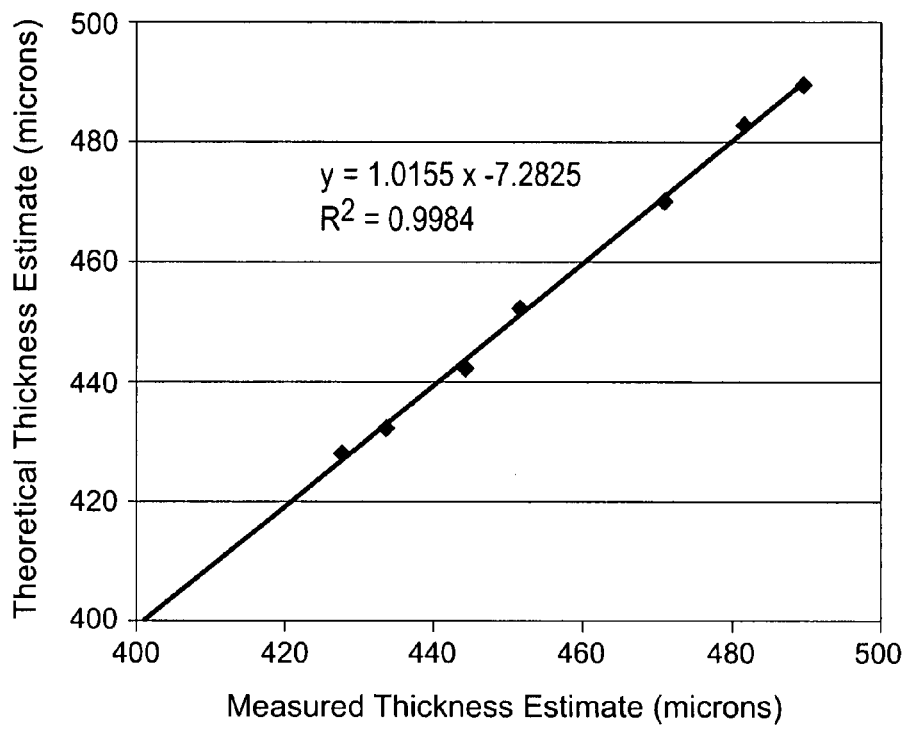
FIG. 7 is a plot of change in diaphragm thickness as calculated using current and Faraday's Law versus the thickness determined from displacement measurements using the mechanics analysis for the corrosivity sensor.

Confirmation of the corrosivity sensor measurements was made by calculating the change in diaphragm thickness from the current (total charge) passed for some time period using Faraday's Law. The thickness obtained from the diaphragm pressure/displacement using Equation 4 was compared to the theoretical thickness loss calculated using Faraday's Law (FIG. 7).

Corrosion tests under galvanostatic control were performed by periodically stepping the pressure to obtain a pressure/displacement (M) measurement. A constant anodic current was applied between the pressure step measurements (FIG. 6). As expected, the reference sensor with the coated steel diaphragm had a relatively constant pressure sensitivity ratio of −0.054 µm/psi; while the corrosivity sensor was strongly dependent on corrosion. The 95% confidence interval for the mean pressure sensitivity of the reference sensor was ±0.0002 µm/psi. The variation in the reference signal was an insignificant source of variation in the corrosivity measurement.

For a starting thickness of the steel diaphragm of 492 µm, the remaining diaphragm thickness was calculated for each time interval of constant current and pressure sensitivity ratio. These two calculated thicknesses based on charge passed and displacement measurements are plotted in FIG. 7. Additionally, these results are raw and not thermally compensated or averaged. The results demonstrate an excellent one to one agreement (slope≈1) and correlation ($R^2$>0.99) between the thickness loss calculated from Faraday's Law and thickness based on the diaphragm displacement, mechanical properties and geometry.

Corrosivity Sensor Response to Free Corrosion

Figure 8:
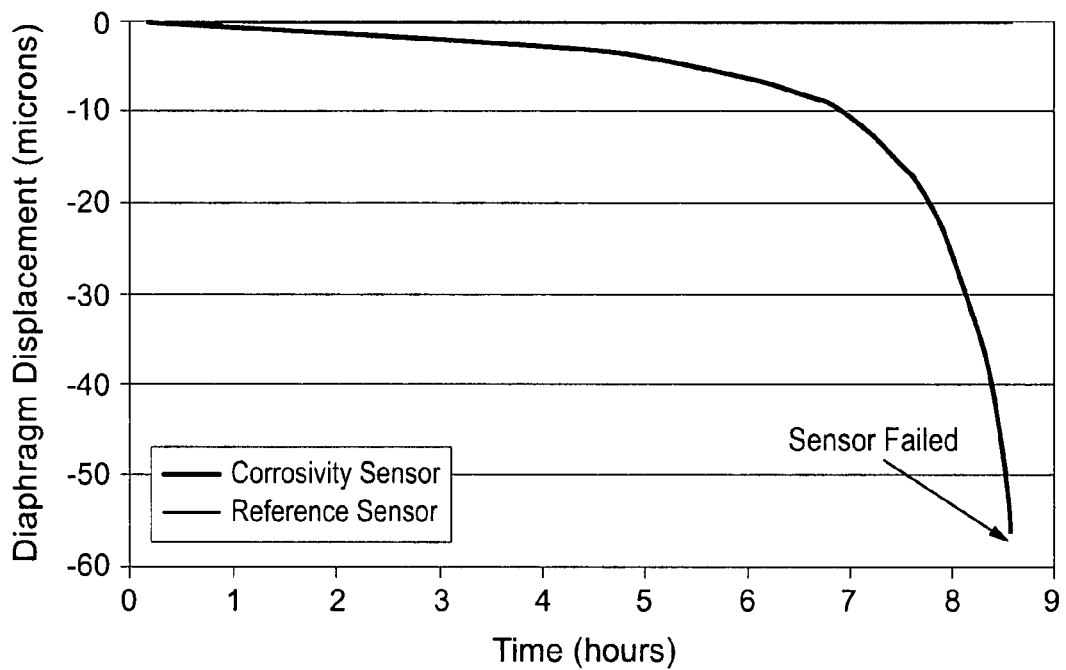
FIG. 8 is a plot of the response of a corrosivity sensor and reference sensor to corrosion in ferric chloride solution with constant applied pressure of 10 psi.

A longer term test was performed on the sensor freely corroding at open circuit conditions. This sensor was identical to the one tested above using current control except that no connection was made between the counter electrode and the test diaphragm. The pressure was maintained at a constant 10 psi throughout the test. The open circuit corrosion produced a continuous change in the corrosivity sensor displacement, and again the reference sensor did not vary as a function of the time (FIG. 8). Conversion of the displacement to diaphragm thickness indicates that the corrosion rate was higher initially, but otherwise relatively constant throughout the test (FIG. 9).

Figure 9:
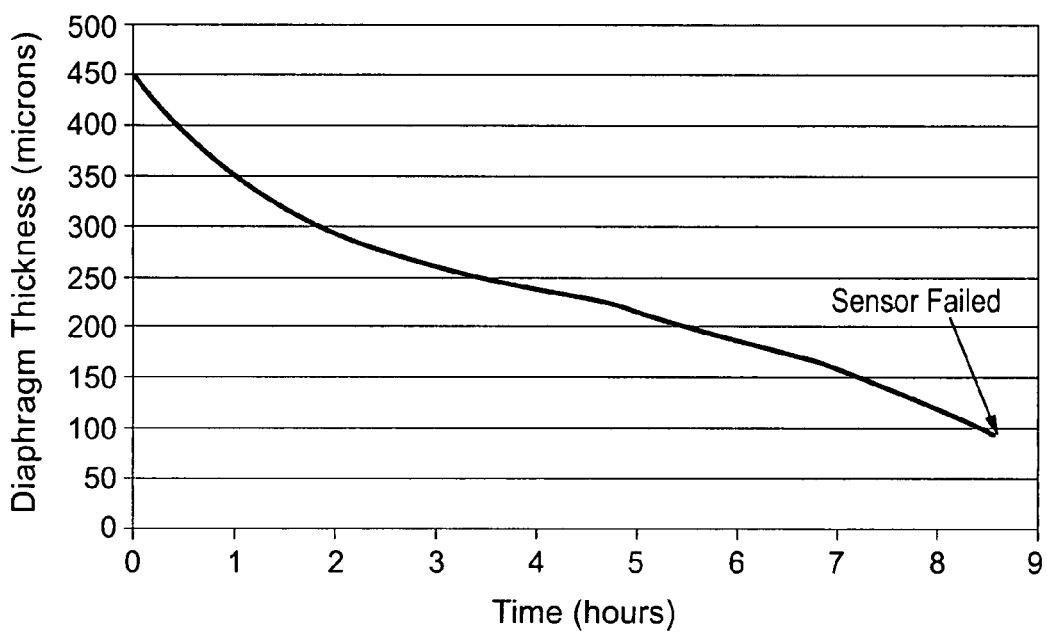
FIG. 9 shows the change in diaphragm thickness of a corrosivity sensor over time, wherein the diaphragm thickness of the corrosivity sensor is calculated from the measured pressure sensitivity.

As shown in FIG. 9, the sensor diaphragm lost approximately 14 mil of thickness (355 microns) prior to failure of the corrosivity sensor. For typical low corrosion rates of 1 MPY to moderate corrosion rates of 10 MPY the sensor lifetime could potential be 14 to 1.4 years, respectively. Electrical based (resistive) sensors are typically designed for 1 year to 3 month replacement intervals. Electrical based (linear polarization resistance) sensors may also require more frequent cleaning or maintenance schedules. The corrosivity sensor according to the present invention usefully provides improved sensitivity, broader applicability and enhanced service life relative to traditional electrical sensing systems.

Summary of Test Results

The results of the testing described above indicate that corrosion rates (corrosivity) in flowing water systems can be monitored using optical fiber based physical effects sensors. Sensor responses measured as diaphragm deflection or displacement/pressure ratio as a function of time were dependent on corrosion rate of the diaphragm. Displacements were used to calculate the thickness loss due to corrosion using a mechanics analysis. The use of diaphragm displacement to measure corrosion rate was validated by comparing the mechanics analysis to the electrochemical measurement of charge passed during the same test period. The one to one relationship and excellent correlation ($R^2$>0.99) between the electrochemical Faraday's Law calculations and the measured thickness as determined by the mechanics model of the corrosivity sensor diaphragm displacement indicate the validity of using the diaphragm response for monitoring changes in mechanical response of the diaphragm to quantify physical effects due to contact with fluid. The ability to use a reference sensor to compensate for other environmental effects, such as temperature, has also been demonstrated. The corrosivity sensor of the present invention therefore is useful to provide improved sensitivity, broader applicability and enhanced service life relative to traditional systems for monitoring corrosivity.

Corrosivity Sensor Compensated with Reference Sensor

A corrosivity and reference sensors as depicted in FIG. 1A were employed for the purpose of this testing. The two sensors were used to produce a corrosion measurement. The reference sensor had constant pressure sensitivity over time, whereas the thinning corrosivity sensor became more sensitive to pressure as it lost thickness. The unknown corrosivity sensor diaphragm thickness can be determined by comparing the relative response of these two sensors to a change in applied pressure using a mechanics approach.

Experimentally and in practice, the two sensors are subjected to the same applied pressure profiles and temperatures. Whenever the pressure exhibits a transient, an opportunity exists to make a corrosion diaphragm thickness measurement. The amplitude of the transient ($\Delta P$) is measured precisely using the reference sensor diaphragm deflection and known pressure calibration. The instrumentation also provides the central deflection of the corrosivity sensor diaphragm ($\Delta y$) for the same transient event. Using the geometry and material properties of the corrosivity sensor diaphragm, one may calculate the effective thickness of the corrosivity sensor diaphragm by Equation 4 above.

The corrosivity sensor diaphragm thickness as a function of time is obtained by repeating the measurement at a defined interval. The thickness versus time curve can be differentiated with respect to time to obtain a measurement of corrosion rate.

Data were collected using the sensor construction and signal processing approach described above under varying corrosivity conditions in a closed test chamber that provided both pressure and electrochemical controls.

The sensors were constructed from 17-4PH SS H1150 for the reference and the corrosivity sensor was fabricated from 1018 cold rolled flat bar. The 17-4PH SS H1150 of the reference sensor is relatively inert in the test environment as compared to the 1018 cold rolled steel of the corrosivity sensor. The corrosivity and reference sensors were machined integral diaphragms. The test environment was 0.6 mM NaCl solution. The applied pressure profile was a 0-50 psi quasi-square wave cycle with a two minute period. The corrosion rate of the corrosivity sensor was controlled using a galvanostat to maintain constant current density. Current is converted to thickness loss as a function of time using Faraday's Law for iron.

Figure 10:
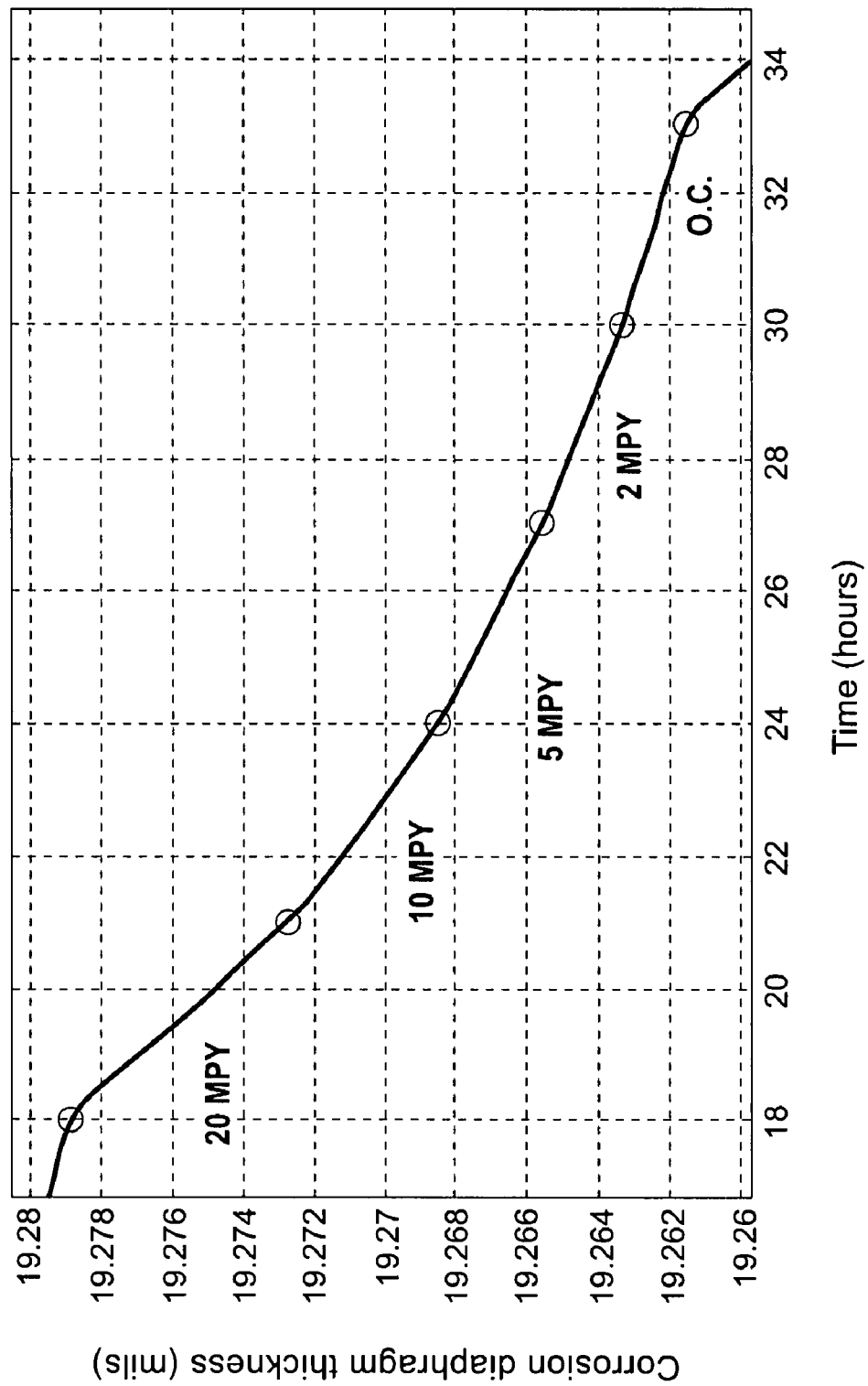
FIG. 10 is a graph of diaphragm thickness of a corrosivity sensor over time with different applied corrosion rates, wherein the diaphragm thickness of the corrosivity sensor is calculated from the change in measured pressure sensitivity relative to a reference sensor.

A representative portion of the test data is shown in FIG. 10. The y-axis is the corrosivity sensor diaphragm thickness in mils (0.001") calculated from the sensor response and the x-axis is elapsed time in hours. The circles superimposed on the test data indicate the times at which the galvanostatic current was switched to different values.

Approximately 100 data points were obtained within each three hour segment of data between current changes. The effective corrosivity diaphragm thickness resolution during this test exceeds 1 microinch. This high resolution allows for rapid assessment of the corrosion rate.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A sensor assembly for determining physical effects over time of a fluid in contact with the physical effects sensor, the sensor comprising:
   a diaphragm for contact with a fluid, the diaphragm exhibiting first and second mechanical responses to first and second actuations of the diaphragm corresponding to first and second time intervals, respectively, wherein a change in the first and second mechanical responses between at least the first and second actuations is indicative of a change of at least one physical effect on the diaphragm over time caused by corrosion, erosion, scaling and/or oxidation of the diaphragm by the fluid in contact therewith; and
   a mechanical response sensor operatively associated with the diaphragm which measures the change in the first and second mechanical responses so as to determine the change of the at least one physical effect on the diaphragm over time caused by corrosion, erosion, scaling and/or oxidation of the diaphragm by the fluid in contact therewith.

2. The physical effects sensor assembly of claim 1, wherein the mechanical response sensor monitors diaphragm deflection, strain or resonant frequency.

3. The physical effects sensor assembly of claim 1, wherein the mechanical response sensor is one selected from optical sensors, piezoelectric sensors, electrical sensors and acoustic sensors.

4. The physical effects sensor assembly of claim 1, wherein the mechanical response of the diaphragm is in response to actuation by a pressure condition exerted thereon by the fluid.

5. The physical effects sensor assembly of claim 1, further comprising an actuator for actively generating the first and second mechanical responses of the diaphragm.

6. The physical effects sensor assembly of claim 5, wherein the actuator comprises a piezoelectric actuator, electromagnetic actuator, pneumatic actuator or a hydraulic actuator.

7. The physical effects sensor assembly of claim 1, wherein the diaphragm is metal or a metal alloy.

8. The physical effects sensor assembly of claim 7, wherein the sensor assembly monitors effects of a fluid on a component formed of a metal or metal alloy, and wherein diaphragm is formed of the same metal or metal alloy as the component.

9. The physical effects sensor assembly of claim 7, wherein the sensor assembly monitors effects of a fluid on a component formed of a metal or metal alloy, and wherein diaphragm is formed of a metal or metal alloy whose physical effects as a result of fluid contact correlate to those of the component.

10. The physical effects sensor assembly of claim 1, further comprising a housing, the diaphragm being operatively fixed to the housing at a distal end thereof so as to establish an exposed front face of the diaphragm which is adapted for contact with the fluid, and a back face of the diaphragm which is located within an interior of the housing.

11. The physical effects sensor assembly of claim 10, wherein at least the first and second mechanical responses are achieved by pressure exerted on the diaphragm from the fluid in contact with the exposed front face of the diaphragm.

12. The physical effects sensor assembly of claim 10, wherein at least the first and second mechanical responses are achieved by direct actuation applied to the back face of the diaphragm.

13. The physical effects sensor assembly of claim 12, wherein the direct actuation is driven by a piezoelectric actuator, electromagnetic actuator, pneumatic actuator or hydraulic actuator.

14. The physical effects sensor assembly of claim 1, further comprising a temperature sensor in operative association with the diaphragm.

15. The physical effects sensor assembly of claim 1 or 14, further comprising at least one reference sensor comprising:
   an inert diaphragm for contact with a fluid, the diaphragm exhibiting first and second mechanical responses to first and second actuations of the inert diaphragm at first and second time intervals, respectively, wherein there is no change in diaphragm mechanical response due to physical effects between at least the first and second actuations over time; and
   a mechanical response sensor operatively associated with the inert diaphragm which measures a change in inert diaphragm mechanical response due to environment factors other than physical effects caused by the fluid in contact therewith.

16. The physical effects sensor assembly of claim 15, wherein the inert diaphragm comprises metal, metal alloy, polymer, glass, or ceramic.

17. The physical effects sensor assembly of claim 15, wherein the inert diaphragm comprises a diaphragm coated with a metal, metal alloy, polymer, glass, or ceramic.

18. The physical effects sensor assembly of claim 1, further comprising an electrochemical sensor in operative association with the physical effects sensor diaphragm.

19. The physical effects sensor assembly of claim 18, wherein the electrochemical method comprises Linear Polarization Resistance (LPR), Electrochemical Impedance Spectroscopy (EIS), galvanic current measurements with a zero resistance ammeter (ZRA), or Electrochemical Noise (EN).

20. A physical effects sensor assembly of claim 1, wherein the fluid is at least one selected from the group consisting of liquid, gas, and a multiphase matter that includes mixtures of solids, gases and/or liquids.

21. A system for measuring physical effects over time of a fluid comprising:
   (i) a sensor assembly as in claim 1, wherein the mechanical response sensor outputs a response signal indicative of the mechanical response of the diaphragm; and
   (ii) a processor for receiving the response signal and outputting a signal indicative of physical effect of the fluid on the diaphragm.

22. The system of claim 21, further comprising a temperature sensor in operative association with the mechanical response sensor.

23. A system of claim 21 or 22, further comprising at least one reference sensor in operative association with the mechanical response sensor.

24. The system of claim 21, wherein the mechanical response sensor detects one of the diaphragm responses selected from deflection, strain, and resonant frequency.

25. The system of claim 21, wherein the mechanical response sensor is one selected from optical sensors, piezoelectric sensors, electrical sensors and acoustic sensors.

26. The system of claim 21, wherein the mechanical response of the diaphragm is in response to actuation by a pressure condition exerted thereon by the fluid.

27. The system of claim 21, further comprising an actuator for actively generating the first and second mechanical responses of the diaphragm.

28. The system of claim 27, wherein the actuator comprises a piezoelectric actuator, electromagnetic actuator, pneumatic actuator or hydraulic actuator.

29. The system of claim 21, wherein the diaphragm is metal or metal alloy.

30. The system of claim 21, further comprising a housing, the diaphragm being operatively fixed to the housing at a distal end thereof so as to establish an exposed front face of the diaphragm which is adapted for contact with the fluid, and a back face of the diaphragm which is located within an interior of the housing.

31. The system of claim 30, wherein at least the first and second mechanical responses are achieved by pressure exerted on the diaphragm from the fluid in contact with the exposed front face of the diaphragm.

32. The system of claim 30, wherein at least the first and second mechanical responses are achieved by direct actuation applied to the back face of the diaphragm.

33. The system of claim 32, wherein the direct actuation is achieved by piezoelectric actuator, electromagnetic actuator, pneumatic actuator or hydraulic actuator.

34. A system for maintaining fluid corrosivity within predetermined corrosivity limits comprising:
   (i) a corrosivity sensor comprising,
      (a) a diaphragm which is susceptible to a change of diaphragm thickness over time due to corrosion when placed in contact with a corrosive fluid, the diaphragm having a mechanical response when actuated which changes over time in correlation with the change of diaphragm thickness due to corrosion of the diaphragm by the fluid, and
      (b) a mechanical response sensor operatively associated with the diaphragm which measures a change in the mechanical response of the diaphragm due to the change of diaphragm thickness and which issues a response signal indicative of the change in the mechanical response;
   (ii) a processor for receiving the response signal and outputting a corrosivity signal indicative of fluid corrosivity; and
   (iii) a controller for receiving the corrosivity signal and controlling a condition of the fluid to maintain fluid corrosivity within predetermined limits.

35. The system of claim 34, wherein the controller controls at least one of temperature and chemical attributes of the fluid in response to receiving the corrosivity signal.

36. The system of claim 34, further comprising a temperature sensor in operative association with the corrosivity sensor.

37. The system of claim 34 or 36, further comprising at least one reference sensor in operative association with the corrosivity sensor.

38. A method of making a physical effects sensor which is capable of sensing physical effects of a fluid comprising the steps of:
   (a) providing a diaphragm which exhibits at least first and second mechanical responses to first and second actuations of the diaphragm corresponding to first and second time intervals, respectively, wherein a change in the first and second mechanical responses between at least the first and second actuations is indicative of a change of at least one physical effect on the diaphragm over time caused by corrosion, erosion, scaling and/or oxidation of the diaphragm by exposure to the fluid in contact therewith; and
   (b) operatively associating a mechanical response sensor with the diaphragm so as to measure the change in the first and second mechanical responses of the diaphragm between at least the first and second time intervals which is indicative of the physical effects on the diaphragm over time caused by corrosion, erosion, scaling and/or oxidation of the diaphragm by the fluid in contact therewith.

39. A method of sensing fluid corrosivity comprising the steps of:
   (a) bringing a sensor assembly into contact with a corrosive fluid, the sensor assembly comprising a diaphragm for contact with a fluid, the diaphragm exhibiting first and second mechanical responses when actuated at respective first and second time intervals, wherein a change in diaphragm mechanical response between at least the first and second actuations is indicative of physical effects on the diaphragm over time caused by the fluid in contact therewith, and a mechanical response sensor operatively associated with the diaphragm which measures the change in diaphragm mechanical response so as to determine the physical effects on the diaphragm over time caused by the fluid in contact therewith;
   (b) exerting an actuation condition on the diaphragm so as to cause the mechanical response of the diaphragm;
   (c) measuring the diaphragm mechanical response;
   (d) calculating thickness change of the diaphragm from the change in measured mechanical response sensitivity;
   (e) deriving fluid corrosivity from the calculated change in diaphragm mechanical response.

40. The method of claim 39, wherein step (c) is practiced by measuring the diaphragm mechanical response with fiber optic sensors or resistive strain gage sensors.

41. The method of claim 39, wherein step (b) is practiced by producing a mechanical response sensor of the diaphragm selected from one of deflection, strain, and resonant frequency.

42. The method of claim 39, wherein step (c) is practiced by an optical sensor, a piezoelectric sensor, an electrical sensor and/or an acoustic sensor.

43. The method of claim 39, wherein the mechanical response of the diaphragm is caused by a pressure condition exerted thereon by the fluid.

44. The method of claim 39, wherein the actuator applied to the back face of the diaphragm for producing a mechanical response of the diaphragm is independent of fluid pressure.

45. The method of claim 44, wherein the actuator comprises a piezoelectric actuator, electromagnetic actuator, pneumatic actuator, or hydraulic actuator.

46. The method of claim 39, wherein the diaphragm is operatively fixed to a distal end of a housing so as to establish an exposed front face of the diaphragm, and a back face of the diaphragm which is located within an interior of the housing, the method comprising bringing the front face of the diaphragm into contact with the fluid.

47. The method claim 46, comprising causing mechanical response of the diaphragm by a pressure condition exerted thereon by the fluid in contact with the exposed front face of the diaphragm.

48. The method of claim 46, comprising producing a mechanical response in the diaphragm by applying actuation to the back face of the diaphragm by means of an actuator.

49. The corrosivity sensor of claim 48, wherein the actuator comprises a piezoelectric actuator, electromagnetic actuator, pneumatic actuator, or hydraulic actuator.

50. A sensor for determining effects of a fluid over time in contact therewith, the sensor comprising:

a diaphragm for contact with a fluid which is susceptible to thinning by the effects of the fluid over time, the diaphragm thereby exhibiting a change in mechanical responses correlated to the thinning when the diaphragm is actuated at respective first and second time intervals; and a mechanical response sensor operatively associated with the diaphragm which measures the change in mechanical responses so as to determine the effects of the fluid over time in contact therewith.

51. A method of sensing effects of a fluid over time, the method comprising:
 (a) placing a diaphragm in contact with a fluid, the diaphragm being susceptible to thinning by the effects of the fluid over time so as to thereby exhibit a change in mechanical responses correlated to the thinning which is indicative of the effects of the fluid over time;
 (b) actuating the diaphragm at respective first and second time intervals; and
 (c) determining the change in the mechanical responses of the diaphragm between the first and second time intervals and thereby sense the effects of the fluid over time.

52. A sensor assembly for determining physical effects of a fluid over time, the sensor assembly comprising:
 (a) a diaphragm for contact with a fluid, the diaphragm being susceptible to a change of diaphragm thickness over time due to the effects of the fluid in contact therewith and having a mechanical response when actuated which changes in correlation with the change of diaphragm thickness over time; and
 (b) a mechanical response sensor operatively associated with the diaphragm which measures a change in the mechanical response of the diaphragm due to the change of diaphragm thickness.

53. The sensor assembly as in claim 52, wherein the mechanical response sensor issues a signal in response to measuring the change in the mechanical response of the diaphragm due to the change of diaphragm thickness, the signal thereby being indicative of the effects of the fluid over time in contact with the diaphragm.

* * * * *